(12) United States Patent
Shuber

(10) Patent No.: US 8,377,657 B1
(45) Date of Patent: Feb. 19, 2013

(54) PRIMERS FOR ANALYZING METHYLATED SEQUENCES AND METHODS OF USE THEREOF

(75) Inventor: Anthony P. Shuber, Mendon, MA (US)

(73) Assignee: Predictive Biosciences Corporation, Lexington, MA (US)

( * ) Notice: Subject to any disclaimer, the term of this patent is extended or adjusted under 35 U.S.C. 154(b) by 0 days.

(21) Appl. No.: 13/472,209

(22) Filed: May 15, 2012

(51) Int. Cl.
*C12P 19/34* (2006.01)
*C07H 21/04* (2006.01)

(52) U.S. Cl. .................. 435/91.2; 536/24.33

(58) Field of Classification Search ............... 435/24.33, 435/91.2
See application file for complete search history.

(56) References Cited

U.S. PATENT DOCUMENTS

| 6,200,756 B1 | 3/2001 | Herman et al. |
| 7,790,385 B2 | 9/2010 | Kutyavin et al. |
| 2005/0009047 A1* | 1/2005 | Erlander et al. .................. 435/6 |
| 2011/0008845 A1 | 1/2011 | Kim et al. |

OTHER PUBLICATIONS

Herman et al., "Methylation-speciifc PCR: A novel PCR assay for methylation status of CpG islands," PNAS, 93: 9821-9826 (1996).
Anglim et al., "DNA methylation-based biomarkers for early detection of non-small cell lung cancer: an update," Molecular Cancer 2008, 7:81.

* cited by examiner

*Primary Examiner* — Gary Benzion
*Assistant Examiner* — Cynthia Wilder
(74) *Attorney, Agent, or Firm* — Thomas C. Meyers; Brown Rudnick LLP

(57) ABSTRACT

Primers having abasic regions or mismatches for amplifying sequences suspected of having methylation. Primers having abasic regions or mismatches for amplifying sequences adjacent to suspected or known methylated sequences. Methods of using primers having abasic regions or mismatches for identification of methylated sequences or sequences adjacent to suspected or known methylation sequences.

8 Claims, 8 Drawing Sheets

```
601 CCACTGTGTAGAAGCTGTTGCCATTGCTGCTGTCACAGCCACTCCGGATGGGGCTGCCAC
    ::|:||||||||||:||||::|||||:||:|||:|:||::|:|:++|||||||:||::|:
601 TTATTGTGTAGAAGTTGTTGTTATTGTTGTTGTTATAGTTATTTCGGATGGGGTTGTTAT
                                                GATGGGGTTGTTAT
                                                Forward 1 (2CpG)

661 CGCGGCCAGGACAGTCTCCTCCGACCGCTTCCTGGGCTGCGCTAGGGTTCGGGGGCGCTG
    ++++|::||||:|||:|::|:++|:++:|||::||||:||++:|||||||++||||++:||
661 CGCGGTTAGGATAGTTTTTTTCGATCGTTTTTGGGTTGCGTTAGGGTTCGGGGGCGTTG
    *G*GGTTAGG           TT*GAT*GTTTTTTGGGTTG  GTTAGGGTT*GGGGG*GTTG
                        Forward 2 (2 CpG)     Forward 3 (2CpG islands)

721 CCCGCACGCTCCGGCGGGGAAGGAAATCGCCCCGCGCCCGCCGGAGGAAGGCGACGGGGA
    ::++:|++:|:++|++|||||||||||++::::++++::++:++|||||||++|++||||
721 TTCGTACGTTTCGGCGGGGAAGGAAATCGTTTCGCGTTCGTCGGAGGAAGGCGACGGGGA
                                                TT*GT*GGAGGAAGG*GA*GG
                                                Reverse 1 (4CpG islands)

781 GGGAAGGGGGAGGGCGGCTAGGAGGCGGGTGGAGGGGCCGGCCGCCCGGGCCAGGTCGTT
    ||||||||||||||++|:|||||||++|||||||||||:++|:++::++|::|||||++||
781 GGGAAGGGGGAGGGCGGTTAGGAGGCGGGTGGAGGGGTCGGTCGTTCGGGTTAGGTCGTT
                   AGGG*GGTTAGGAGG*GGG     T*GGT*GTT*GGGTTAGGT*GT
                   Reverse 2 (2 CpG)           Reverse 3 (4 CpG)
```

FIG. 1

```
1621 TCATCCTCTCATCCGGGCTGCCCCGCGGCCCCCAAGGAGCCCCACCCCCGGGACCAAATG
     |:||::|:|:||:++||:||:::++++|:::::||||||::::|::::++||::||||
1621 TTATTTTTTTATTCGGGTTGTTTCGCGGTTTTTAAGGAGTTTTATTTTCGGGATTAAATG
     TTTTTTTATT*GGGTTG      G*GGTTTTTAAGGAGTTTTATTTT*
       Forward 4 (1CpG)        Forward 5 (2CpG islands)

1681 GCCCGCAAGGTTTGGGGCAGCGGCGTTGCAGGAGATGAGCTCAGCGCAAAGGGAACCCCG
     |::++|||||||||||:||++|++|||:||||||||||:|:||++:||||||||:::++
1681 GTTCGTAAGGTTTGGGGTAGCGGCGTTGTAGGAGATGAGTTTAGCGTAAAGGGAATTTCG
     T*GTAAGGTTTGGGGTAG*GG              AG*GTAAAGGGAATTT*G
       Forward 6 (2CpG)                   Reverse 4 (2CpG islands)

1741 CAGCGGCGAGTGCGGCTGCTGGCCTGCGCGCTGTGGCCCCAACAGGCTGGCAGGGCGCGG
     :||++|++|||++|:||:|||::||++++:||||::::||:|||:|||:||||++++|
1741 TAGCGGCGAGTGCGGTTGTTGGTTTGCGCGTTGTGGTTTTAATAGGTTGGTAGGGCGCGG
     TAG*GG*GAGTG*GGTTG                 AGGTTGGTAGGG*G*GG
       Reverse 5 (3CpG)                   Reverse 6 (2CpG)
```

FIG. 2

```
601 CCACTGTGTAGAAGCTGTTGCCATTGCTGCTGTCACAGCCACTCCGGATGGGGCTGCCAC
    ::|:||||||||||:||||::||||:|:|||:|:||::|:|:++|||||||:||::|:
601 TTATTGTGTAGAAGTTGTTGTTATTGTTGTTGTTATAGTTATTTCGGATGGGGTTGTTAT
```
Forward 7 (2CpG)

```
661 CGCGGCCAGGACAGTCTCCTCCGACCGCTTCCTGGGCTGCGCTAGGGTTCGGGGGCGCTG
    ++++|::||||:|||:|:::|:++|:++:||::||||:||++:||||||++||||++:||
661 CGCGGTTAGGATAGTTTTTTCGATCGTTTTTGGGTTGCGTTAGGGTTCGGGGGCGTTG
```
Forward 8 (2 CpG)   Forward 9(2CpG islands)

```
721 CCCGCACGCTCCGGCGGGGAAGGAAATCGCCCCGCGCCCGCCGGAGGAAGGCGACGGGGA
    ::++:|++:|:++|++||||||||||++:::++++::++:++||||||||++|++||||
721 TTCGTACGTTTCGGCGGGGAAGGAAATCGTTTCGCGTTCGTCGGAGGAAGGCGACGGGGA
```
Reverse 7(4CpG islands)

```
781 GGGAAGGGGGAGGGCGGCTAGGAGGCGGGTGGAGGGGCCGGCCGCCCGGGCCAGGTCGTT
    |||||||||||||++|:||||||||++|||||||||||:++|:++::++|::||||++||
781 GGGAAGGGGGAGGGCGGTTAGGAGGCGGGTGGAGGGGTCGGTCGTTCGGGTTAGGTCGTT
```
Reverse 8 (2 CpG)   Reverse 9 (4 CpG)

FIG. 3

```
1621 TCATCCTCTCATCCGGGCTGCCCCGCGGCCCCCAAGGAGCCCCACCCCCGGGACCAAATG
     |:||::|:|:||:++||:||:::++++|:::::||||::::|::::++|||::||||
1621 TTATTTTTTTATTCGGGTTGTTTCGCGGTTTTTAAGGAGTTTTATTTTCGGGATTAAATG
     TTTTTTTATTNGGGTTG    GNGGTTTTTAAGGAGTTTTATTTTN
        Forward 10 (1CpG)      Forward 11 (2CpG islands)

1681 GCCCGCAAGGTTTGGGGCAGCGGCGTTGCAGGAGATGAGCTCAGCGCAAAGGGAACCCCG
     |::++:||||||||||||:||++|++|||:|||||||||:|:||++:|||||||:::++
1681 GTTCGTAAGGTTTGGGGTAGCGGCGTTGTAGGAGATGAGTTTAGCGTAAAGGGAATTTCG
     TNGTAAGGTTTGGGGTAGNGG                AGNGTAAAGGGAATTTNG
        Forward 12 (2CpG)                 Reverse 10 (2CpG islands)

1741 CAGCGGCGAGTGCGGCTGCTGGCCTGCGCGCTGTGGCCCCAACAGGCTGGCAGGGCGCGG
     :||++|++|||++|:||:|||::|++++:||||::::||:|||:|||:||||++++|
1741 TAGCGGCGAGTGCGGTTGTTGGTTTGCGCGTTGTGGTTTTAATAGGTTGGTAGGGCGCGG
     TAGNGGNGACTGNGGTTG                   AGGTTGGTAGGGNGNGG
        Reverse 11 (3CpG)                    Reverse 12 (2CpG)
```

FIG. 4

```
601 CCACTGTGTAGAAGCTGTTGCCATTGCTGCTGTCACAGCCACTCCGGATGGGGCTGCCAC
    ::|:||||||||:|||||::|||:||:|||:|:||::|:|:++|||||||:||::|:
601 TTATTGTGTAGAAGTTGTTGTTATTGTTGTTGTTATAGTTATTTCGGATGGGGTTGTTAT

661 CGCGGCCAGGACAGTCTCCTCCGACCGCTTCCTGGGCTGCGCTAGGGTTCGGGGGCGCTG
    ++++|::||||:|||:|::|:++|:++:|||::||||:||++:|||||||++|||++:||
661 CGCGGTTAGGATAGTTTTTTTCGATCGTTTTTGGGTTGCGTTAGGGTTCGGGGGCGTTG
                          TTT*GAT*GTTTTTTGGGTTG
                          Forward A4

721 CCCGCACGCTCCGGCGGGGAAGGAAATCGCCCCGCGCCCGCCGGAGGAAGGCGACGGGGA
    ::++:|++:|:++|++|||||||||||||++|::++++::++:++|||||||++|++|||
721 TTCGTACGTTTCGGCGGGGAAGGAAATCGTTTCGCGTTCGTCGGAGGAAGGCGACGGGGA
                                                              GA

781 GGGAAGGGGGAGGGCGGCTAGGAGGCGGGTGGAGGGGCCGGCCGCCCGGGCCAGGTCGTT
    ||||||||||||||++|:|||||||++||||||||||:++|:++::++|::|||||++||
781 GGGAAGGGGGAGGGCGGTTAGGAGGCGGGTGGAGGGGTCGGTCGTTCGGGTTAGGTCGTT
    GGGAAGGGGGAGGG
    Reverse SM REV 1
```

FIG. 5

```
1621 TCATCCTCTCATCCGGGCTGCCCCGCGGCCCCCAAGGAGCCCCACCCCCGGGACCAAATG
     |:||::|:|:||:++||:||::::++++|:::::|||||||::::|::::++|||::||||
1621 TTATTTTTTATTCGGGTTGTTTCGCGGTTTTTAAGGAGTTTTATTTTCGGGATTAAATG
     TTTTTTTATT GGGTTGTTT
              Forward A3
```

```
1681 GCCCGCAAGGTTTGGGGCAGCGGCGTTGCAGGAGATGAGCTCAGCGCAAAGGGAACCCCG
     |::++:||||||||||:||++|++||:|||||||||:|:||++:|||||||||:::++
1681 GTTCGTAAGGTTTGGGGTAGCGGCGTTGTAGGAGATGAGTTTAGCGTAAAGGGAATTTCG
```

```
1741 CAGCGGCGAGTGCGGCTGCTGGCCTGCGCGCTGTGGCCCCAACAGGCTGGCAGGGCGCGG
     :||++|++|||++|:||:|||::||++++:||||::::|:|||:|||:|||++++|
1741 TAGCGGCGAGTGCGGTTGTTGGTTTGCGCGTTGTGGTTTTAATAGGTTGGTAGGGCGCGG
                                   GTTGTGGTTTTAATAGGTTG
                                   Reverse SM REV3
```

PRIMERS FOR ANALYZING METHYLATED SEQUENCES AND METHODS OF USE THEREOF

FIELD OF THE INVENTION

The present invention generally relates to a primers configured to specifically hybridize to either a methylated or an unmethylated CpG site of a template nucleic acid or adjacent to a methylated or an unmethylated CpG site of a template nucleic acid, and methods of use thereof.

BACKGROUND

DNA methylation is an important regulator of gene expression and may play a role in the development and progression of a number of diseases, such as cancer. Methylation is typically limited to cytosines located 5' to a guanine (i.e., CpG sequences), however other forms of methylation are known. Research suggests that genes with high levels of methylation in a promoter region are transcriptionally silent, which may allow unchecked cell proliferation.

When a promoter region has excessive methylation, the methylation is typically most prevalent in sequences having CpG repeats, so called "CpG islands." Undermethylation (hypomethylation) has also been implicated in the development and progression of cancer through different mechanisms.

Several methods have been developed to identify and quantify methylation, especially in CpG sites, e.g., CpG islands, that are implicated in silencing promoters. Those include sequencing methods in which genomic DNA is isolated and treated with bisulfite. Because methylated cytosines are not affected by bisulfite treatment, the unmethylated Cs, e.g., within a CpG site, are converted to uracil, while methylated Cs are not converted. After sequencing, comparison of the starting DNA and the bisulfate treated DNA indicates the location of methylation sites.

Perhaps the most widely-used method of probing methylation patterns is methylation specific PCR (MSP) which uses two sets of primers for an amplification reaction. One primer set is complimentary to sequences whose Cs are converted to Us by bisulfite treatment, and the other primer set is complimentary to non-converted Cs. Using these two separate primer sets, both the methylated and unmethylated DNA are amplified. Comparison of the amplification products gives insight as to the methylation in a given sequence. See Herman et al., "Methylation-specific PCR: A novel PCR assay for methylation status of CpG islands," *P.N.A.S.*, vol. 93, p. 9821-26 (1996), which is incorporated herein by reference in its entirety. This technique can detect methylation changes as small as ±0.1%. In addition to methylation of CpG islands, many of the sequences surrounding clinically relevant hypermethylated CpG islands can also be hypermethylated, and are potential biomarkers.

A problem with MSP is that it requires the use of two different primer sets, one for sequences containing methylated Cs, and the other for sequences containing Us, which were converted from unmethylated Cs by bisulfite treatment. Using two different primer sets limits the application of MSP. In addition to the costs associated with producing and maintaining two separate primer sets, the amplification process cannot be maximally efficient because of the need to operate in temperature regimes appropriate for both primer sets.

SUMMARY

The invention provides compositions and methods for performing methylation specific amplification of nucleic acids using a single primer set. Aspects of the invention are accomplished by using primers configured such that they are able to specifically hybridize to either a methylated or an unmethylated site, e.g., a CpG island, of a template nucleic acid. Aspects of the invention are also accomplished by using primers configured such that they are able to specifically hybridize adjacent to a methylated or an unmethylated site, e.g., a CpG island, of a template nucleic acid. Accordingly, there is no need to have different primer sequences that distinguish between converted uracil sequences and unconverted cytosine sequences. Thus, amplification reactions are performed on nucleic acid with a single set of primers, which reduces costs and lowers assay complexity.

One way that this is accomplished is by providing primers that include an abasic region that interacts with either the methylated or the unmethylated CpG site of the template nucleic acid. For example, a primer may contain one or more abasic regions corresponding to expected locations of methylation sites. Often the abasic region will be linked to a guanine moiety. The primer may contain any known abasic (spacer) molecule that is known in the art. Another way to accomplish this goal is to provide primers including at least one mismatched nucleotide that has similar annealing characteristics to both uracil and cytosine such that the primer hybridizes to either the methylated or the unmethylated CpG site of the template nucleic acid. Another way to accomplish this goal is to provide primers that hybridize to sequences adjacent to methylated or the unmethylated CpG site(s) of the template nucleic acid. The primer set allows for amplification of the entire site. Analysis of the amplification products gives information about the methylation status of the sample.

In some embodiments, the primers may include an adaptor sequence such that amplicons are produced with adaptors already attached. In other embodiments, adaptors are attached to the amplicons after the amplification reaction. The adaptor sequence may optionally include a homopolymer region, e.g., a poly-A region. In some embodiment, the primer can specifically hybridize to either the methylated or the unmethylated CpG site of the template nucleic acid under conditions of high stringency. In some instances, it is useful to use sequencing to analyze the amplification products. In these embodiments it may be helpful to have a universal adaptor on the amplicons so that they can be hybridized to a universal primer on a solid support for the sequencing reaction.

Primers of the invention may be used in a number of applications where it is desirable to analyze methylation of a sequence, e.g., epigenetics or diagnosing a disease, e.g., cancer. For example, a methylation pattern of a nucleic acid may be analyzed by obtaining template nucleic acid, contacting the template nucleic acid with an agent (e.g., bisulfite) that modifies unmethylated cytosine, hybridizing a primer configured such that it is able to specifically hybridize to either a methylated or an unmethylated CpG site of the template nucleic acid, amplifying the template nucleic acid, and analyzing a methylation pattern of the amplified nucleic acid. Any amplification or analysis method may be used in the methods of the invention. For example, PCR amplification, direct sequencing, fluorescent probe hybridization, etc. In some instances, the template nucleic acid is amplified with PCR. In some instances, the amplified nucleic acid in analyzed by sequencing the nucleic acid.

BRIEF DESCRIPTION OF THE DRAWINGS

FIG. 1 depicts a TWIST sequence with various regions of potential methylation, and forward and reverse primers having abasic regions which can be used to amplify the TWIST sequence;

FIG. 2 depicts a NID sequence with various regions of potential methylation, and forward and reverse primers having abasic regions which can be used to amplify the NID sequence;

FIG. 3 depicts a TWIST sequence with various regions of potential methylation, and forward and reverse primers having mismatches which can be used to amplify the TWIST sequence;

FIG. 4 depicts a NID sequence with various regions of potential methylation, and forward and reverse primers having mismatches which can be used to amplify the NID sequence;

FIG. 5 depicts a TWIST sequence with various regions of potential methylation, and forward and reverse primers which can be used to amplify CpG islands within the TWIST sequence;

FIG. 7 depicts a NID sequence with various regions of potential methylation, and forward and reverse primers which can be used to amplify CpG islands within the NID sequence;

DETAILED DESCRIPTION

Figure 6:
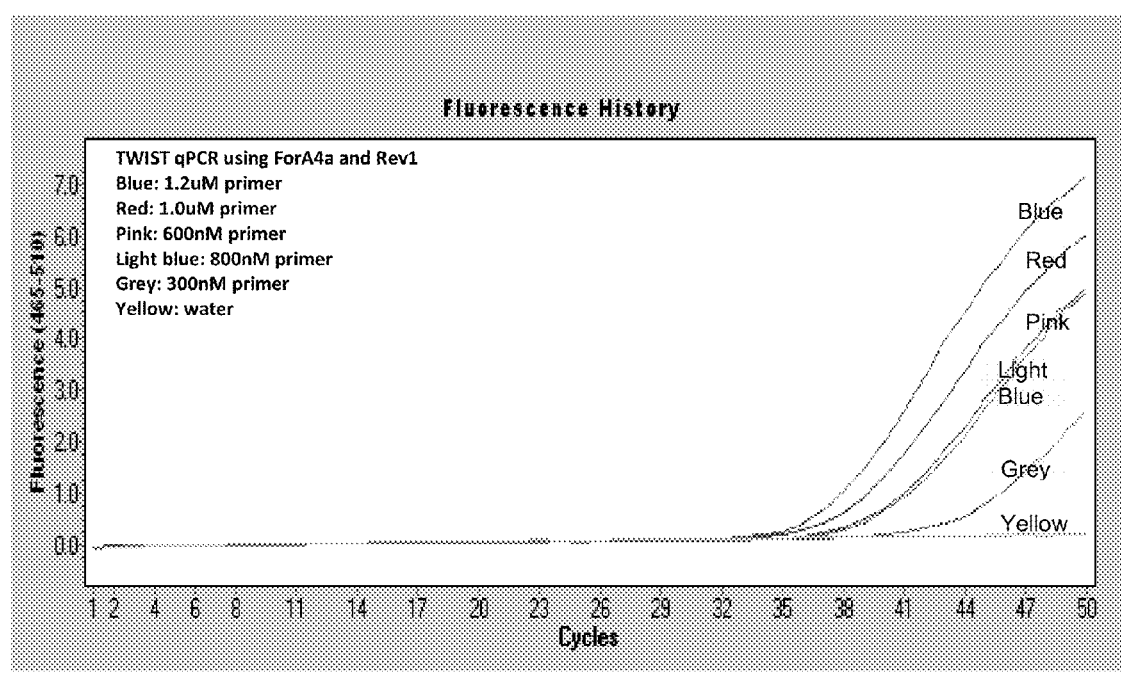
FIG. 6 shows fluorescence intensity due to production of amplification products as a function of the concentration of the primers shown in FIG. 5.

The present invention generally relates to primers configured to able to specifically hybridize to either a methylated or an unmethylated site, e.g., a CpG site, e.g., a CpG island of a template nucleic acid, or to hybridize adjacent to a methylated or an unmethylated site, and methods of use thereof. In certain aspects, the invention provides a primer configured such that it is able to specifically hybridize to either a methylated or an unmethylated CpG site of a template nucleic acid.

Methylation generally refers to cytosine methylation at positions C5 or N4 of cytosine, the N6 position of adenine or other types of nucleic acid methylation. In some embodiments, methylation is analyzed by treating a nucleic acid sequence with bisulfate and then comparing the sequences of the bisulfite-treated and untreated nucleic acid sequences to identify one or more methylation regions. In some embodiments, methylation is detected using methylation specific polymerase chain reaction.

DNA methylation is a chemical modification of DNA performed by enzymes called methyltransferases, in which a methyl group (m) is added to certain cytosines (C) of DNA, to yield 5-methylcytosine. This non-mutational (epigenetic) process (mC) is a critical factor in gene expression regulation. See, e.g., J. G. Herman, *Seminars in Cancer Biology*, 9: 359-67, 1999. Research suggests genes with high levels of 5-methylcytosine in a promoter region are transcriptionally silent, which allows unchecked cell proliferation. Additionally, it is likely that there a correlation between gene transcription and undermethylation.

Methylation appears to influence gene expression by affecting the interactions with DNA of both chromatin proteins and specific transcription factors. 5-Methylcytosine performs much like a regular cytosine, pairing up with a guanine. However, some areas of genome are methylated more heavily than others and highly methylated areas tend to be less transcriptionally active, through a mechanism not fully understood. Methylation of cytosines can also persist from the germ line of one of the parents into the zygote, marking the chromosome as being inherited from this parent (genetic imprinting). DNA methylation frequently occurs in repeated sequences, e.g., CpG islands, and helps to suppress the expression and mobility of transposable elements. Because 5-methylcytosine is chemically very similar to thymidine, CpG sites are frequently mutated and become rare in the genome, except at CpG islands where they remain unmethylated. Epigenetic changes of this type thus have the potential to direct increased frequencies of permanent genetic mutation.

Methylation patterns of DNA from cancer cells are significantly different from those of normal cells. Therefore, detection of methylation patterns in appropriately selected genes of cancer cells can lead to discrimination of cancer cells from normal (i.e., non-cancerous) cells, thereby providing an approach to early detection of cancer.

A common method for assessing methylation status, e.g., the presence of CpG islands, is methylation specific PCR, also known as MSP. In MSP a nucleic acid sample is treated with a methylation reactant, typically bisulfite, and then amplified in the presence of two sets of primers. One primer set is complimentary to sequences with converted Cs and the second primer set is complimentary to non-converted Cs. Using these two separate primer sets, both the methylated and unmethylated DNA can be simultaneously amplified, and the amplification products compared (e.g., sequenced) to determine methylation sites in a given sequence. The MSP method, and variations on the MSP method, are described in greater detail in U.S. Pat. Nos. 6,265,171, 6,331,393, 6,977, 146, 7,186,512, and 7,229,759 all of which are incorporated by reference herein in their entireties.

As stated, the methods are useful for detecting the methylation status of at least one gene. This generally means determining the presence or absence of 5-methylcytosine at one or a plurality of (functionally relevant) CpG dinucleotides within the DNA sequence of the at least one gene. In particular, aberrant methylation, which may be referred to as hypermethylation, of the at least one gene may be detected. Typically, the methylation status is determined in one or more CpG sites, e.g., CpG islands in the at least one gene. These CpG sites are often found in the promoter region of the gene(s). Thus, CpG dinucleotides are typically concentrated in the promoter regions and exons of human genes and the methylation status of these CpG residues is of functional importance to whether the at least one gene is expressed. Since CpG dinucleotides susceptible to methylation are typically concentrated in the promoter region, exons and introns of human genes, promoter, exon and intron regions may be assessed in order to determine the methylation status of the at least one gene. A "promoter" is a region extending typically between approximately 1 Kb, 500 by or 150 to 300 by upstream from the transcription start site. The CpG site may surround or be positioned around the transcription start site of the at least one gene.

In some embodiments, methods for detecting methylation status rely upon a reagent which selectively modifies unmethylated cytosine residues in the DNA contained in the sample to produce detectable modified residues but which does not modify methylated cytosine residues. Any suitable reagent may be utilized in the methods of the invention. Examples include bisulphite, hydrogen sulphite and disulphite reagents and suitable mixtures thereof. In an embodiment of the invention, the reagent comprises, consists essentially of or consists of a bisulphite reagent. In some embodiments, the invention includes primers having an abasic region and a region complementary to a template having a methylated CpG sequence or a UpG sequence. In some embodiments, the abasic region of the primer may only span one base of the template, for example, a C of a CpG sequence that is likely to be methylated. However, the invention includes primers whose abasic region spans more than one base, for example three or five bases. Primers of the invention may also include more than one abasic region, for example, a first abasic region separated by sequence consisting of A, C, T, and G, and then a second abasic region. The primer could comprise less than about 20, less than about 15, less than about 10, less than about 8, less than about 6, less than about 5, less than about 4, or less than about 3 abasic regions. The primer could comprise less than about 80%, less than about 60%, less than about 50%, less than about 30%, less than about 20%, less than about 15%, less than about 10%, less than about 5%, or less than about 2% of the sequence comprises abasic regions. A number of suitable primer sequences are disclosed, however, the concept is generally applicable to any primer sequence that would be used to analyze for methylation of a nucleic acid strand, e.g., to investigate methylation in a template.

The invention additionally provides kits for providing a set of abasic primers for use in analyzing methylated sequences. For example, such a kit might include a reaction buffer, a DNA polymerase, and a primer having an abasic region and a region complementary to a template having a methylated CpG sequence or a UpG sequence. Some kits may additionally include a set of deoxyribonucleotides needed for the amplification.

Using the primers or the kits above, it is possible to amplify a template suspected of having a methylated cytosine through a series of steps including: 1) providing a template suspected of having a methylated cytosine, 2) providing a primer having an abasic region and a region complementary to a template having a methylated CpG sequence or a UpG sequence, 3) mixing the template and the primer in the presence of free deoxyribonucleotides; and, 4) amplifying the template using PCR techniques. Once the template has been amplified, the amplified template can be isolated and sequenced. Typically the template suspected of having a methylated cytosine will be contacted with a bisulfite solution prior to the amplification in order to convert unmethylated Cs to Us.

The invention additionally relates to primers having a sequence complementary to a template having a methylated CpG sequence or a UpG sequence, the primer having at least one mismatched base corresponding to a cytosine in the methylated CpG sequence or a uracil in the UpG sequence. These mismatches would be chosen to have similar annealing characteristics to Us and Cs and specific to the PCR technique used. Following the first few cycles of the PCR, the mismatched base(s) will become incorporated in the amplified product and subsequent annealing cycles would not involve a mismatched base, rather, the primer becomes a perfect match for amplified templates. Using these primers, it is no longer necessary to have two different primer sets that distinguish between bisulfite converted sequences and unconverted sequences when performing methylation analysis. In an embodiment, primary PCR reactions can be performed on genomic DNA with a single set of primers, followed by sequencing to identify and quantify clinically relevant sequences nested between the PCR primers.

In some embodiments, the mismatched bases of the primer may only span one base of the template, for example, a C of a CpG sequence that is likely to be methylated. However, the invention includes primers whose mismatched bases span more than one base, for example three or five bases. Primers of the invention may also include more than one group of mismatches, for example, a first mismatched base separated by sequence consisting of A, C, T, and G, and then a second mismatched base. The primer could comprise less than about 20, less than about 15, less than about 10, less than about 8, less than about 6, less than about 5, less than about 4, or less than about 3 mismatched bases. The primer could comprise less than about 80%, less than about 60%, less than about 50%, less than about 30%, less than about 20%, less than about 15%, less than about 10%, less than about 5%, or less than about 2% of the sequence comprises mismatched bases. A number of suitable primer sequences are disclosed, however, the concept is generally applicable to any primer sequence that would be used for amplification (e.g., MSP) or to investigate methylation in a nucleic acid strand.

The present invention also relates to kits for providing a set of primers having mismatched bases for use in MSP. For example, such a kit might include a reaction buffer, a DNA polymerase, and a primer including a sequence complementary to a template having a methylated CpG sequence or a UpG sequence, the primer having at least one mismatched base corresponding to a cytosine in the methylated CpG sequence or a uracil in the UpG sequence. Some kits may additionally include a set of deoxyribonucleotides needed for the amplification.

Using the primers or the kits of the invention, it is possible to amplify a template suspected of having a methylated cytosine through a series of steps including: 1) providing a template suspected of having a methylated cytosine, 2) providing a primer having a sequence complementary to a template having a methylated CpG sequence or a UpG sequence, the primer having at least one mismatched base corresponding to a cytosine in the methylated CpG sequence or a uracil in the UpG sequence, 3) mixing the template and the primer in the presence of free deoxyribonucleotides; and, 4) amplifying the template using PCR techniques. Once the template has been amplified, the amplified template can be isolated and sequenced. Typically the template suspected of having a methylated cytosine will be contacted with a bisulfite solution prior to the amplification in order to convert unmethylated Cs to Us.

These mismatches would be chosen to have similar annealing characteristics to Us and Cs and specific PCR. Following the first few cycles of the PCR, the mismatched base(s) become incorporated in the amplified product and subsequent annealing cycles do not involve a mismatched base, but it is now a perfect match. This approach also eliminates the necessity to perform a primary PCR with different primers that are complimentary to bisulfite converted and unconverted primer sequences.

Primers of the invention are designed to be substantially complementary to each template (i.e., strand of the oligonucleotide to be amplified). In other words, the primers should have sufficient complementarity with a 5' and 3' oligonucleotide to hybridize and permit amplification of a nucleic acid sequence suspected to be at least partially methylated, e.g., including a CpG sequence.

Primers of the invention are employed in the amplification process, which is an enzymatic chain reaction that produces exponentially increasing quantities of template relative to the number of reaction steps involved (e.g., polymerase chain reaction or PCR). Typically, one primer is complementary to a template corresponding to a negative (−) strand of the locus of interest, the antisense primer, and the other is complementary a template corresponding to the positive (+) strand, the sense primer. Annealing the primers to denatured nucleic acid followed by extension with an enzyme, such as the large fragment of DNA Polymerase I and nucleotides, results in newly synthesized + and − strands containing the target locus sequence. Because these newly synthesized sequences are also templates, repeated cycles of denaturing, primer annealing, and extension results in exponential production of the region (i.e., the target locus sequence) defined by the primer. The product of the chain reaction is a discrete nucleic acid duplex with termini corresponding to the ends of the specific primers employed.

Suitable conditions for primer extension are readily determined by those skilled in the art. These conditions include incubation temperature, incubation time, assay reagents, stabilizing factors, polymerizing agent, pH, and ionic strength sufficient to promote base pairing between the primer and desired template or target sequence. Polymerizing agents include enzymes capable of extending a primer by adding or substituting a nucleotide or modified nucleotide at the 3' end of the primer. Suitable polymerizing enzymes include all manner of nucleotide polymerases.

Polymerases may be isolated or cloned from a variety of organisms including viruses, bacteria, archaebacteria, fungi, mycoplasma, prokaryotes, and eukaryotes. Polymerases exhibiting thermal stability may also be employed, such as for example, polymerases from *Thermus* species, including *Thermus aquaticus, Thermus brocianus, Thermus thermophilus*, and *Thermus flavus; Pyrococcus* species, including *Pyrococcus furiosus, Pyrococcus* sp. GB-D, and *Pyrococcus woesei, Thermococcus litoralis*, and *Thermogata maritime*. Biologically active proteolytic fragments, recombinant polymerases, genetically engineered polymerizing enzymes, and modified polymerases are included in the definition of polymerizing agent. It should be understood that the invention can employ various types of polymerases from various species and origins without undue experimentation.

Suitable conditions for primer extension include hybridization and stringency conditions allowing desired hybridization between the primer and template or target sequence. As used herein, two nucleic acid sequences are said to be capable of specifically hybridizing to one another if the two molecules are capable of forming an anti-parallel, double-stranded nucleic acid structure or hybrid under hybridizing conditions, whereas they are substantially unable to form a double-stranded structure or hybrid when incubated with a non-target nucleic acid sequence under the same conditions. A nucleic acid molecule is said to be the "complement" of another nucleic acid molecule if it exhibits complete Watson-Crick base pair complementarity. Two molecules are said to be "substantially complementary" if they can hybridize to one another with sufficient stability to permit them to remain annealed to one another under at least conventional low-stringency conditions. Similarly, the molecules are said to be "complementary" if they can hybridize to one another with sufficient stability to permit them to remain annealed to one another under conventional high-stringency conditions. Stringency conditions in referring to homology or substantial similarity in the hybridization context, can be combined conditions of salt, temperature, organic solvents or other parameters that are typically known to influence hybridization. Typically, high stringency conditions include conditions selected to be 5 or more degrees higher than the thermal melting point (Tm) for a specific sequence at a defined ionic strength and pH. The Tm is the temperature (under defined ionic strength and pH) at which 50% of the target sequence hybridizes to a perfectly matched sequence. These techniques are well known in the art. For example, conventional stringency conditions are described in Sambrook, J., et al., *Molecular Cloning, a Laboratory Manual,* 2nd Edition, Cold Spring Harbor Press, Cold Spring Harbor, N.Y. (1989), and Haymes, B. D., et al., Nucleic Acid Hybridization, A Practical Approach, IRL Press, Washington, D.C. (1985), both of which are incorporated by reference in their entireties.

Primers can be prepared by a variety of methods including but not limited to cloning of appropriate sequences and direct chemical synthesis using methods well known in the art (Narang et al., Methods Enzymol. 68:90 (1979); Brown et al., Methods Enzymol. 68:109 (1979)). Primers can also be obtained from commercial sources such as Operon Technologies, Amersham Pharmacia Biotech, Sigma, Integrated DNA Technologies, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The $T_m$ (melting or annealing temperature) of each primer is calculated using software programs such as Oligo Design, available from Invitrogen Corp.

The annealing temperature of the primers can be recalculated and increased after any cycle of amplification, including but not limited to cycle 1, 2, 3, 4, 5, cycles 6-10, cycles 10-15, cycles 15-20, cycles 20-25, cycles 25-30, cycles 30-35, or cycles 35-40. After the initial cycles of amplification, the 5' half of the primers is incorporated into the products from each loci of interest, thus the $T_m$ can be recalculated based on both the sequences of the 5' half and the 3' half of each primer.

A primer of the invention may contain an abasic region or a mismatch at any position on the primer, provided that the primer is stable enough to endure the thermocycling of PCR amplification and provided that the primer does not self-anneal. A number of abasic regions are commercially available from suppliers, such as Integrated DNA Technologies, and can be custom incorporated into primer sequences. Exemplary abasic regions include, but are not limited to, O-dimethoxytrityl-1',2'-dideoxyribose-3'-[(2-cyanoethyl)-(N,N-diisopropyl)]-phosphoramidite, O-dimethoxytrityl-1'-methoxy-2'-dideoxyribose-3'-[(2-cyanoethyl)-(N,N-diisopropyl)]-phosphoramidite, [4-(4,4'-Dimethoxytrityloxy)butyramidomethyl)-1-(2-nitrophenyl)-ethyl]-2-cyanoethyl-(N,N-diisopropyl)-phosphoramidite, O-Dimethoxytrityl-1'-Deoxyribose-2'-O-Triisopropylsilyloxymethyl-3'-[(2-cyanoethyl)-(N,N-diisopropyl)]-phosphoramidite, (4,4'-Dimethoxytrityloxy)-dodecyl-1-[(2-cyanoethyl)-(N,N-diisopropyl)]-phosphoramidite), O-Dimethoxytritylhexaethyleneglycol,1-[(2-cyanoethyl)-(N,N-diisopropyl)]-phosphoramidite, O-Dimethoxytrityl-triethyleneglycol,1-[(2-cyanoethyl)-(N,N-diisopropyl)]-phosphoramidite; and 3-(4,4'-Dimethoxytrityloxy)propyl-1-[(2-cyanoethyl)-(N,N-diisopropyl)]-phosphoramidite.

Primers containing mismatches can be ordered from any commercial supplier, e.g., Integrated DNA Technologies, provided that at least one mismatch is incorporated corresponding to a suspected methylation site. These mismatches would be chosen to have similar annealing characteristics to Us and Cs and specific to the PCR technique used.

A number of exemplary sequences are shown in FIGS. 1-4, including both forward and reverse primers, including both abasic regions and mismatches. In FIGS. 1-4 the top sequence is listed 5' to 3', thus the lower sequence and the primers are listed 3' to 5'. FIG. 1 shows abasic forward and reverse primers suitable for amplifying portions of a sequence coding a TWIST gene. The "+" symbols indicate regions that are likely to have methylation. Forward primers include SEQ ID NO. 1: 3'-GATGGGGTTGTTAT*G*GGTTAGG-5'; SEQ ID NO. 2:

3'-TT*GAT*GTTTTTTGGGTTG-5'; and SEQ ID NO. 3: 3'-GTTAGGGTT*GGGGG*GTTG-5', wherein "*" is an abasic region spanning one base of the template. Reverse primers include SEQ ID NO. 4: 3'-TT*GT*GGAGGAAGG*GA*GG-5'; SEQ ID NO. 5: 3'-AGGG*GGTTAGGAGG*GGG-5'; and SEQ ID NO. 6: 3'-T*GGT*GTT*GGGTTAGGT*GT-5', wherein "*" is an abasic region spanning one base of the template.

FIG. 2 shows abasic forward and reverse primers suitable for amplifying portions of a sequence coding a NID gene. The "+" symbols indicate regions that are likely to have methylation. Forward primers include SEQ ID NO. 7: 3'-TTTTTTTATT*GGGTTG-5'; SEQ ID NO. 8: 3'-G*GGTTTTTAAGGAGTTTTATTTT*-5'; and SEQ ID NO. 9: 3'-T*GTAAGGTTTGGGGTAG*GG-5', wherein "*" is an abasic region spanning one base of the template. Reverse primers include SEQ ID NO. 10: 3'-AG*GTAAAGGGAATTT*G-5'; SEQ ID NO. 11: 3'-TAG*GG*GAGTG*GGTTG-5'; and SEQ ID NO. 12: 3'-AGGTTGGTAGGG*G*GG-5', wherein "*" is an abasic region spanning one base of the template.

FIG. 3 shows mismatched forward and reverse primers suitable for amplifying portions of a sequence coding a TWIST gene. The "+" symbols indicate regions that are likely to have methylation. Forward primers include SEQ ID NO. 13: 3'-GATGGGGTTGTTATNGNGGTTAGG-5'; SEQ ID NO. 14: 3'-TTNGATNGTTTTTTGGGTTG-5'; and SEQ ID NO. 15: 3'-GTTAGGGTTNGGGGGNGTTG-5', wherein "N" is a single mismatched base. Reverse primers include SEQ ID NO. 16: 3'-TTNGTNGGAGGAAGGNGANGG-5'; SEQ ID NO. 17: 3'-AGGGNGGTTAGGAGGNGGG-5'; and SEQ ID NO. 18: 3'-TNGGTNGTTNGGGTTAGGTNGT-5', wherein "N" is a single mismatched base.

FIG. 4 shows mismatched forward and reverse primers suitable for amplifying portions of a sequence coding a NID gene. The "+" symbols indicate regions that are likely to have methylation. Forward primers include SEQ ID NO. 19: 3'-TTTTTTTATTNGGGTTG-5'; SEQ ID NO. 20: 3'-GNGGTTTTTAAGGAGTTTTATTTTN-5'; and SEQ ID NO. 21: 3'-TNGTAAGGTTTGGGGTAGNGG-5', wherein "N" is a single mismatched base. Reverse primers include SEQ ID NO. 22: 3'-AGNGTAAAGGGAATTTNG-5'; SEQ ID NO. 23: 3'-TAGNGGNGAGTGNGGTTG-5'; and SEQ ID NO. 24: 3'-AGGTTGGTAGGGNGNGG-5', wherein "N" is a single mismatched base.

In some embodiments, the primers of the invention will additionally include a label. The label may be directly attached to the primer or the label may be attached via a linker, for example a polymer linker. The label attached to the primer may be directly or indirectly detectable. In certain embodiments, the exact label may be selected based, at least in part, on the particular type of detection method used. Exemplary detection methods include radioactive detection, optical absorbance detection, e.g., UV-visible absorbance detection, optical emission detection, e.g., fluorescence, phosphorescence, chemiluminescence, or Raman scattering. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl] naphthalimide-3,5 disulfonate; N-(4-anilino-1-naphthyl)maleimide; anthranilamide; BODIPY; alexa; fluorescien; conjugated multi-dyes; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'tetramethyl-6-carboxyrhodamine (TAMRA); tetramethyl rhodamine; tetramethyl rhodamine isothiocyanate (TRITC); riboflavin; rosolic acid; terbium chelate derivatives; Atto dyes, Cy3; Cy5; Cy5.5; Cy7; IRD 700; IRD 800; La Jolla Blue; phthalo cyanine; and naphthalo cyanine. Labels other than fluorescent labels are contemplated by the invention, including other optically-detectable labels.

In some embodiments, the amplicons produced with the disclosed methods include a detectable barcode-type label to facilitate sorting of amplified products. A detectable barcode-type label can be any barcode-type label known in the art including, for example, radio-frequency tags, semiconductor chips, barcoded magnetic beads (e.g., from Applied Biocode, Inc., Santa Fe Springs, Calif.), and nucleic acid sequences. When assessing methylation status, it may be useful to incorporate a barcode into a nucleic acid amplification product that is suspected to have methylation at a CpGsite, or is adjacent to a methylation site.

In some instances, primers may include a barcode such that the barcode will be incorporated into the amplified produces. For example, the unique barcode sequence could be incorporated into the 5' end of the primer, or the barcode sequence could be incorporated into the 3' end of the primer. The primers may additionally comprise adaptors, e.g., as discussed below, such that the adaptors are incorporated into the amplified products.

In alternate embodiments, the barcodes and/or the adaptors may be incorporated into the amplified products after amplification. For example, a suitable restriction enzyme (or other endonuclease) may be used to cut off an end of an amplification product so that a barcode can be added with a ligase. The same steps may be used to add an adaptor, e.g., a universal adaptor to the amplification products. These methods provide additional functionality for later processes, for example, sorting and sequencing.

Attaching barcode sequences to nucleic acids is shown in U.S. Pub. 2008/0081330 and PCT/US09/64001, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety.

Barcode sequences typically include a set of oligonucleotides ranging from about 4 to about 20 oligonucleotide bases (e.g., 8-10 oligonucleotide bases), which uniquely encode a discrete library member preferably without containing significant homology to any sequence in the targeted genome. The barcode sequence generally includes features useful in sequencing reactions. For example the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence. In certain embodiments, the barcode sequences are designed to be correlated to a particular subject, allowing subject samples to be distinguished. Designing barcodes is shown U.S. Pat. No. 6,235,475, the contents of which are incorporated by reference herein in their entirety.

In certain embodiments, the barcode sequences range from about 2 nucleotides to about nucleotides, e.g., about 5 nucleotides to about 10 nucleotides. Since the barcode sequence is sequenced along with the template nucleic acid to which it is attached, the oligonucleotide length should be of minimal length so as to permit the longest read from the template nucleic acid attached. Generally, the barcode sequences are spaced from the template nucleic acid molecule by at least one base (minimizes homopolymeric combinations).

In certain embodiments adaptor oligonucleotides are included in the primers. In some embodiments, the adaptors include a homopolymer region, e.g., a region of poly(A) or poly(T), that can hybridize to a universal primer for the sequence reaction. See also Sabot et al. (U.S. patent application number 2009/0226975), Adessi et al. (U.S. Pat. No. 7,115,400), and Kawashima et al. (U.S. patent application number 2005/0100900), the content of each of which is incorporated by reference herein in its entirety. Any method known in the art may be used to join the adaptors with the primers, for example, a ligase, a polymerase, Topo cloning (e.g., Invitrogen's topoisomerase vector cloning system using a topoisomerase enzyme), or chemical ligation or conjugation. The ligase may be any enzyme capable of ligating an oligonucleotide (RNA or DNA) to the primers. Suitable ligases include T4 DNA ligase and T4 RNA ligase (such ligases are available commercially, from New England Biolabs). Methods for using ligases are well known in the art. The polymerase may be any enzyme capable of adding nucleotides to the 3' and the 5' terminus of template nucleic acid molecules.

Generally, a set of primers of the invention, including a forward and a reverse primer, may be substituted for one or more set(s) of primers used in methylation identification and analysis techniques of the art. In addition to PCR, primers may also be used in quantitative ("real-time") PCR (qPCR), which allows for quantitative analysis of specific sequences during the amplification. A method for using PCR to assess methylation of a group of CpG sites within a CpG island by using two sets of primers is described in U.S. Pat. No. 6,017,704 incorporated by reference herein in its entirety. Primer sets of the invention are generally compatible with other PCR protocols described in the literature.

In the example of MSP, primers specific for templates with methylated Cs, and Cs that have been converted to Us after contacting the template with bisulfite, are used in PCR. By comparing the amplification products of the two primer reactions, it is possible to distinguish between the chemically modified methylated and unmethylated DNA, which adds an improved sensitivity of methylation detection. In addition, MSP eliminates the false positive results inherent to other PCR-based approaches which rely on differential restriction enzyme cleavage to distinguish methylated from unmethylated DNA. MSP also allows examination of all CpG sites, not just those within sequences recognized by methylation-sensitive restriction enzymes. This markedly increases the number of such sites which can be assessed and will allow rapid, fine mapping of methylation patterns throughout CpG rich regions.

The primers of the invention may be used for sensitive and specific test for detecting and diagnosing different diseases or disorders, particularly diseases or disorders associated with hypermethylation, particularly cancer. In some embodiments, it is possible to detect and diagnose a disease or disorder using only MSP. In some embodiments, the assessment a disease or disorder requires a combination of different types of assays, e.g., in addition to MSP.

In some embodiments a sample is only analyzed for methylation. In other embodiments, both a sequence mutation and abnormal methylation are analyzed from a patient sample. The sequence mutation and the abnormal methylation may occur on the same chromosome, or on different chromosomes. Optionally, one or more chromosomal abnormalities (e.g., chromosomal instability) may be detected in combination with a sequence mutation and abnormal methylation to further improve diagnostic accuracy.

Methods of the invention involve obtaining a biological sample, from a subject. Samples may include any bodily fluid such as blood, a blood fraction, saliva, sputum, urine, semen, transvaginal fluid, cerebrospinal fluid, or stool. Other such samples may include one or more cells or a tissue biopsy, such as a cell or biopsy from the brain, mouth, throat, esophagus, stomach, lymph node, stomach, intestine (large or small), kidney, bladder, liver, pancreas, skin, muscle, bone, bone marrow, breast, ovary, vagina, cervix, uterus, testicle or prostate.

The sample may be obtained by methods known in the art, such as a phlebotomy, cheek swab, fine needle aspiration, core needle biopsy, vacuum assisted biopsy, direct and frontal lobe biopsy, shave biopsy, punch biopsy, excisional biopsy, or cutterage biopsy. Once the sample is obtained, nucleic acids are extracted to assess nucleic acid sequence mutations, chemical sequence modifications, and/or chromosomal abnormalities.

Primers of the invention may be prepared so that they hybridize under high stringency conditions. Nucleic acid hybridization may be affected by such conditions as salt concentration, temperature, or organic solvents, in addition to base composition, length of complementary strands, and number of nucleotide base mismatches between hybridizing nucleic acids, as is readily appreciated by those skilled in the art. Stringency of hybridization reactions is readily determinable by one of ordinary skill in the art, and generally is an empirical calculation dependent upon sequence length, washing temperature, and salt concentration. In general, longer sequences require higher temperatures for proper annealing, while shorter sequences need lower temperatures. Hybridization generally depends on the ability of denatured DNA to reanneal when complementary strands are present in an environment below its melting temperature. The higher the degree of desired homology between the sequence and hybridizable sequence, the higher the relative temperature that can be used.

As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995), the contents of which are incorporated by reference herein in their entirety.

Stringent conditions or high stringency conditions typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 .mu.g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1× SSC containing EDTA at 55° C.

Moderately stringent conditions may be identified as described by Sambrook et al., Molecular Cloning: A Laboratory Manual, New York: Cold Spring Harbor Press, 1989 (the contents of which are incorporated by reference herein in their entirety), and include the use of washing solution and hybridization conditions (e.g., temperature, ionic strength and % SDS) less stringent that those described above. An example of moderately stringent conditions is overnight incubation at 37° C. in a solution including: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37° C. to 50° C. The skilled artisan will recognize how to adjust the temperature, ionic strength, etc. as necessary to accommodate factors such as sequence length and the like.

In other embodiments, primers of the invention may be prepared and hybridized under low stringency conditions. For example, a primer of the invention may contain a relatively large number of abasic regions or mismatches, and/or it may be desirable to have the primer anneal with a diverse set of target sequences, e.g., when the target sequence is not known. In general the conditions for hybridization can be adjusted to obtain specificity suitable for the application.

Nucleic acids may be obtained by methods known in the art. Generally, nucleic acids can be extracted from a biological sample by a variety of techniques such as those described by Maniatis, et al., Molecular Cloning: A Laboratory Manual, Cold Spring Harbor, N.Y., pp. 280-281, (1982), the contents of which is incorporated by reference herein in its entirety. The isolated nucleic acid molecules may be single-stranded, double-stranded, or double-stranded with single-stranded regions (for example, stem- and loop-structures). The isolated nucleic acid can be deoxyribonucleic acid (DNA) and/or ribonucleic acid (RNA). In a particular embodiment, genomic DNA is isolated from the biological sample.

It may be necessary to first prepare an extract of the cell and then perform further steps—i.e., differential precipitation, column chromatography, extraction with organic solvents and the like—in order to obtain a sufficiently pure preparation of nucleic acid. Extracts may be prepared using standard techniques in the art, for example, by chemical or mechanical lysis of the cell.

Extracts then may be further treated, for example, by filtration and/or centrifugation and/or with chaotropic salts such as guanidinium isothiocyanate or urea or with organic solvents such as phenol and/or HCCl3 to denature any contaminating and potentially interfering proteins.

In a particular, primers of the invention may be used for screening for the presence or absence of methylation of a nucleic acid sequence, such as de-methylation, methylation, hypomethylation and hypermethylation. Any one or combination of methods may be used for detecting methylation as well as the different types of genetic markers from the patient's isolated nucleic acid. Suitable methods include real-time or quantitative PCR, digital PCR, PCR in flowing or stationary droplets, well plates, slugs or fluid flowing segments, and the like, in capillary tubes, microfluidic chips, or standard thermocycler based PCR methods known to those having ordinary skill in the art. Additional detection methods can utilize binding to microarrays for subsequent fluorescent or non-fluorescent detection, barcode mass detection using a mass spectrometric methods, detection of emitted radiowaves, detection of scattered light from aligned barcodes, fluorescence detection using quantitative PCR or digital PCR methods.

Still other techniques include, for example, Northern blot, selective hybridization, cleaved amplified polymorphic sequence analysis, short tandem repeat analysis, the use of supports coated with oligonucleotide probes, amplification of the nucleic acid by RT-PCR, quantitative PCR or ligation-PCR, etc. These methods can include the use of a nucleic acid probe (for example, an oligonucleotide) that can selectively or specifically detect the target nucleic acid in the sample to detect changes at the level of a single nucleotide polymorphism, whole DNA-fingerprint analysis, allele specific analysis. Amplification is accomplished according to various methods known to the person skilled in the art, such as PCR, LCR, transcription-mediated amplification (TMA), strand-displacement amplification (SDA), NASBA, the use of allele-specific oligonucleotides (ASO), allele-specific amplification, Southern blot, single-strand conformational analysis (SSCA), in-situ hybridization (e.g., FISH), migration on a gel, heteroduplex analysis, etc. If necessary, the quantity of nucleic acid detected can be compared to a reference value, for example a median or mean value observed in patients who do not have cancer, or to a value measured in parallel in a non-cancerous sample. Thus, it is possible to demonstrate a variation in the level of expression.

In some embodiments, amplified templates will be sequenced. Sequencing may be achieved by any method known in the art. DNA sequencing techniques include classic di-deoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, polony sequencing, and SOLiD sequencing. Sequencing of separated molecules has more recently been demonstrated by sequential or single extension reactions using polymerases or ligases as well as by single or sequential differential hybridizations with libraries of probes.

In certain embodiments, the target nucleic acid or the amplified nucleic acid or both are detected using sequencing. Sequencing-by-synthesis is a common technique used in next generation procedures and works well with the instant invention. However, other sequencing methods can be used, including sequence-by-ligation, sequencing-by-hybridization, gel-based techniques and others. In general, sequencing involves hybridizing a primer to a template to form a template/primer duplex, contacting the duplex with a polymerase in the presence of a detectably-labeled nucleotides under conditions that permit the polymerase to add nucleotides to the primer in a template-dependent manner. Signal from the detectable label is then used to identify the incorporated base and the steps are sequentially repeated in order to determine the linear order of nucleotides in the template. Exemplary detectable labels include radiolabels, florescent labels, enzymatic labels, etc. In particular embodiments, the detectable label may be an optically detectable label, such as a fluorescent label. Exemplary fluorescent labels include cyanine, rhodamine, fluorscien, coumarin, BODIPY, alexa, or conjugated multi-dyes. Numerous techniques are known for detecting sequences and some are exemplified below. However, the exact means for detecting and compiling sequence data does not affect the function of the invention described herein.

A sequencing technique that can be used in the methods of the provided invention includes, for example, Helicos True Single Molecule Sequencing (tSMS) (Harris T. D. et al. (2008) Science 320:106-109). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/cm$^2$. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step. Further description of tSMS is shown for example in Lapidus et al. (U.S. Pat. No. 7,169,560), Lapidus et al. (U.S. patent application number 2009/0191565), Quake et al. (U.S. Pat. No. 6,818,395), Harris (U.S. Pat. No. 7,282,337), Quake et al. (U.S. patent application number 2002/0164629), and Braslavsky, et al., PNAS (USA), 100: 3960-3964 (2003), the contents of each of these references is incorporated by reference herein in its entirety.

Another example of a DNA sequencing technique that can be used in the methods of the provided invention is 454 sequencing (Roche) (Margulies, M et al. 2005, Nature, 437, 376-380). 454 sequencing involves two steps. In the first step, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

Another example of a DNA sequencing technique that can be used in the methods of the provided invention is SOLiD technology (Applied Biosystems). In SOLiD sequencing, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

Another example of a DNA sequencing technique that can be used in the methods of the provided invention is Ion Torrent sequencing (U.S. patent application numbers 2009/0026082, 2009/0127589, 2010/0035252, 2010/0137143, 2010/0188073, 2010/0197507, 2010/0282617, 2010/0300559), 2010/0300895, 2010/0301398, and 2010/0304982), the content of each of which is incorporated by reference herein in its entirety. In Ion Torrent sequencing, DNA is sheared into fragments of approximately 300-800 base pairs, and the fragments are blunt ended. Oligonucleotide adaptors are then ligated to the ends of the fragments. The adaptors serve as primers for amplification and sequencing of the fragments. The fragments can be attached to a surface and is attached at a resolution such that the fragments are individually resolvable. Addition of one or more nucleotides releases a proton ($H^+$), which signal detected and recorded in a sequencing instrument. The signal strength is proportional to the number of nucleotides incorporated.

Another example of a sequencing technology that can be used in the methods of the provided invention is Illumina sequencing. Illumina sequencing is based on the amplification of DNA on a solid surface using fold-back PCR and anchored primers. Genomic DNA is fragmented, and adapters are added to the 5' and 3' ends of the fragments. DNA fragments that are attached to the surface of flow cell channels are extended and bridge amplified. The fragments become double stranded, and the double stranded molecules are denatured. Multiple cycles of the solid-phase amplification followed by denaturation can create several million clusters of approximately 1,000 copies of single-stranded DNA molecules of the same template in each channel of the flow cell.

Primers, DNA polymerase and four fluorophore-labeled, reversibly terminating nucleotides are used to perform sequential sequencing. After nucleotide incorporation, a laser is used to excite the fluorophores, and an image is captured and the identity of the first base is recorded. The 3' terminators and fluorophores from each incorporated base are removed and the incorporation, detection and identification steps are repeated.

Another example of a sequencing technology that can be used in the methods of the provided invention includes the single molecule, real-time (SMRT) technology of Pacific Biosciences. In SMRT, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is repeated.

Another example of a sequencing technique that can be used in the methods of the provided invention is nanopore sequencing (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

Another example of a sequencing technique that can be used in the methods of the provided invention involves using a chemical-sensitive field effect transistor (chemFET) array to sequence DNA (for example, as described in US Patent Application Publication No. 20090026082). In one example of the technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

Another example of a sequencing technique that can be used in the methods of the provided invention involves using a electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

Sequences can be read that originate from a single molecule or that originate from amplifications from a single molecule. Millions of independent amplifications of single molecules can be performed in parallel either on a solid surface or in tiny compartments in water/oil emulsion. The DNA sample to be sequenced can be diluted and/or dispersed sufficiently to obtain one molecule in each compartment. This dilution can be followed by DNA amplification to generate copies of the original DNA sequences and creating "clusters" of molecules all having the same sequence. These clusters can then be sequenced. Many millions of reads can be generated in one run. Sequence can be generated starting at the 5' end of a given strand of an amplified sequence and/or sequence can be generated from starting from the 5' end of the complementary sequence. In a preferred embodiment, sequence from strands is generated, i.e. paired end reads (see for example, Harris, U.S. Pat. No. 7,767,400).

Nucleotides useful in the invention include any nucleotide or nucleotide analog, whether naturally-occurring or synthetic. For example, preferred nucleotides include phosphate esters of deoxyadenosine, deoxycytidine, deoxyguanosine, deoxythymidine, adenosine, cytidine, guanosine, and uridine. Other nucleotides useful in the invention include an adenine, cytosine, guanine, thymine base, a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, locked nucleic acids and any other structural moiety that can act substantially like a nucleotide or base, for example, by exhibiting base-complementarity with one or more bases that occur in DNA or RNA and/or being capable of base-complementary incorporation, and includes chain-terminating analogs. A nucleotide corresponds to a specific nucleotide species if they share base-complementarity with respect to at least one base.

Nucleotides for nucleic acid sequencing according to the invention preferably include a detectable label that is directly or indirectly detectable. Preferred labels include optically-detectable labels, such as fluorescent labels. Examples of fluorescent labels include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Ciba-cron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

Nucleic acid polymerases generally useful in the invention include DNA polymerases, RNA polymerases, reverse transcriptases, and mutant or altered forms of any of the foregoing. DNA polymerases and their properties are described in detail in, among other places, DNA Replication 2nd edition, Kornberg and Baker, W. H. Freeman, New York, N.Y. (1991). Known conventional DNA polymerases useful in the invention include, but are not limited to, *Pyrococcus furiosus* (Pfu) DNA polymerase (Lundberg et al., 1991, Gene, 108: 1, Stratagene), *Pyrococcus woesei* (Pwo) DNA polymerase (Hinnisdaels et al., 1996, Biotechniques, 20:186-8, Boehringer Mannheim), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent™ DNA polymerase, Cariello et al., 1991, Polynucleotides Res, 19: 4193, New England Biolabs), 9.degree.Nm™ DNA polymerase (New England Biolabs), Stoffel fragment, ThermoSequenase® (Amersham Pharmacia Biotech UK), Therminator™ (New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), DNA polymerase, *Pyrococcus kodakaraensis* KOD DNA polymerase (Takagi et al., 1997, Appl. Environ. Microbiol. 63:4504), JDF-3 DNA polymerase (from *thermococcus* sp. JDF-3, Patent application WO 0132887), *Pyrococcus* GB-D (PGB-D) DNA polymerase (also referred as Deep Vent™ DNA polymerase, Juncosa-Ginesta et al., 1994, Biotechniques, 16:820, New England Biolabs), U1Tma DNA polymerase (from thermophile *Thermotoga maritima*; Diaz and Sabino, 1998 Braz J. Med. Res, 31:1239; PE Applied Biosystems), Tgo DNA polymerase (from *thermococcus gorgonarius*, Roche Molecular Biochemicals), *E. coli* DNA polymerase I (Lecomte and Doubleday, 1983, Polynucleotides Res. 11:7505), T7 DNA polymerase (Nordstrom et al., 1981, J. Biol. Chem. 256:3112), and archaeal DP1I/DP2 DNA polymerase II (Cann et al, 1998, Proc. Natl. Acad. Sci. USA 95:14250).

Both mesophilic polymerases and thermophilic polymerases are contemplated. Thermophilic DNA polymerases include, but are not limited to, ThermoSequenase®, 9.degree.Nm™, Therminator™, Taq, Tne, Tma, Pfu, Tfl, Tth, Tli, Stoffel fragment, Vent™ and Deep Vent™ DNA polymerase, KOD DNA polymerase, Tgo, JDF-3, and mutants, variants and derivatives thereof. A highly-preferred form of any polymerase is a 3' exonuclease-deficient mutant.

Reverse transcriptases useful in the invention include, but are not limited to, reverse transcriptases from HIV, HTLV-1, HTLV-II, FeLV, FIV, SIV, AMV, MMTV, MoMuLV and other retroviruses (see Levin, Cell 88:5-8 (1997); Verma, Biochim Biophys Acta. 473:1-38 (1977); Wu et al., CRC Crit. Rev Biochem. 3:289-347 (1975)).

In a preferred embodiment, nucleic acid template molecules are attached to a substrate (also referred to herein as a surface) and subjected to analysis by single molecule sequencing as described herein. Nucleic acid template molecules are attached to the surface such that the template/primer duplexes are individually optically resolvable. Substrates for use in the invention can be two- or three-dimensional and can include a planar surface (e.g., a glass slide) or can be shaped. A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites.

Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a nucleic acid. Substrates can include planar arrays or matrices capable of having regions that include populations of template nucleic acids or primers. Examples include nucleoside-derivatized CPG and polystyrene slides; derivatized magnetic slides; polystyrene grafted with polyethylene glycol, and the like.

Substrates are preferably coated to allow optimum optical processing and nucleic acid attachment. Substrates for use in the invention can also be treated to reduce background. Exemplary coatings include epoxides, and derivatized epoxides (e.g., with a binding molecule, such as an oligonucleotide or streptavidin).

Various methods can be used to anchor or immobilize the nucleic acid molecule to the surface of the substrate. The immobilization can be achieved through direct or indirect bonding to the surface. The bonding can be by covalent linkage. See, Joos et al., Analytical Biochemistry 247:96-101, 1997; Oroskar et al., Clin. Chem. 42:1547-1555, 1996; and Khandjian, Mol. Bio. Rep. 11:107-115, 1986. A preferred attachment is direct amine bonding of a terminal nucleotide of the template or the 5' end of the primer to an epoxide integrated on the surface. The bonding also can be through non-covalent linkage. For example, biotin-streptavidin (Taylor et al., J. Phys. D. Appl. Phys. 24:1443, 1991) and digoxigenin with anti-digoxigenin (Smith et al., Science 253:1122, 1992) are common tools for anchoring nucleic acids to surfaces and parallels. Alternatively, the attachment can be achieved by anchoring a hydrophobic chain into a lipid monolayer or bilayer. Other methods for known in the art for attaching nucleic acid molecules to substrates also can be used.

Any detection method can be used that is suitable for the type of label employed. Thus, exemplary detection methods include radioactive detection, optical absorbance detection, e.g., UV-visible absorbance detection, optical emission detection, e.g., fluorescence or chemiluminescence. For example, extended primers can be detected on a substrate by scanning all or portions of each substrate simultaneously or serially, depending on the scanning method used. For fluorescence labeling, selected regions on a substrate may be serially scanned one-by-one or row-by-row using a fluorescence microscope apparatus, such as described in Fodor (U.S. Pat. No. 5,445,934) and Mathies et al. (U.S. Pat. No. 5,091, 652). Devices capable of sensing fluorescence from a single molecule include scanning tunneling microscope (siM) and the atomic force microscope (AFM). Hybridization patterns may also be scanned using a CCD camera (e.g., Model TE/CCD512SF, Princeton Instruments, Trenton, N.J.) with suitable optics (Ploem, in Fluorescent and Luminescent Probes for Biological Activity Mason, T. G. Ed., Academic Press, Landon, pp. 1-11 (1993), such as described in Yershov et al., Proc. Natl. Acad. Sci. 93:4913 (1996), or may be imaged by TV monitoring. For radioactive signals, a phosphorimager device can be used (Johnston et al., Electrophoresis, 13:566, 1990; Drmanac et al., Electrophoresis, 13:566, 1992; 1993). Other commercial suppliers of imaging instruments include General Scanning Inc., (Watertown, Mass. on the World Wide Web at genscan.com), Genix Technologies (Waterloo, Ontario, Canada; on the World Wide Web at confocal.com), and Applied Precision Inc. Such detection methods are particularly useful to achieve simultaneous scanning of multiple attached template nucleic acids.

A number of approaches can be used to detect incorporation of fluorescently-labeled nucleotides into a single nucleic acid molecule. Optical setups include near-field scanning microscopy, far-field confocal microscopy, wide-field epi-illumination, light scattering, dark field microscopy, photoconversion, single and/or multiphoton excitation, spectral wavelength discrimination, fluorophor identification, evanescent wave illumination, and total internal reflection fluorescence (TIRF) microscopy. In general, certain methods involve detection of laser-activated fluorescence using a microscope equipped with a camera. Suitable photon detection systems include, but are not limited to, photodiodes and intensified CCD cameras. For example, an intensified charge couple device (ICCD) camera can be used. The use of an ICCD camera to image individual fluorescent dye molecules in a fluid near a surface provides numerous advantages. For example, with an ICCD optical setup, it is possible to acquire a sequence of images (movies) of fluorophores.

Some embodiments of the present invention use TIRF microscopy for imaging. TIRF microscopy uses totally internally reflected excitation light and is well known in the art. See, e.g., the World Wide Web at nikon-instruments.jp/eng/page/products/tirf.aspx. In certain embodiments, detection is carried out using evanescent wave illumination and total internal reflection fluorescence microscopy. An evanescent light field can be set up at the surface, for example, to image fluorescently-labeled nucleic acid molecules. When a laser beam is totally reflected at the interface between a liquid and a solid substrate (e.g., a glass), the excitation light beam penetrates only a short distance into the liquid. The optical field does not end abruptly at the reflective interface, but its intensity falls off exponentially with distance. This surface electromagnetic field, called the "evanescent wave", can selectively excite fluorescent molecules in the liquid near the interface. The thin evanescent optical field at the interface provides low background and facilitates the detection of single molecules with high signal-to-noise ratio at visible wavelengths.

The evanescent field also can image fluorescently-labeled nucleotides upon their incorporation into the attached template/primer complex in the presence of a polymerase. Total internal reflectance fluorescence microscopy is then used to visualize the attached template/primer duplex and/or the incorporated nucleotides with single molecule resolution.

Some embodiments of the invention use non-optical detection methods such as, for example, detection using nanopores (e.g., protein or solid state) through which molecules are individually passed so as to allow identification of the molecules by noting characteristics or changes in various properties or effects such as capacitance or blockage current flow (see, for example, Stoddart et al, Proc. Nat. Acad. Sci., 106: 7702, 2009; Purnell and Schmidt, ACS Nano, 3:2533, 2009; Branton et al, Nature Biotechnology, 26:1146, 2008; Polonsky et al, U.S. Application 2008/0187915; Mitchell & Howorka, Angew. Chem. Int. Ed. 47:5565, 2008; Borsenberger et al, J. Am. Chem. Soc., 131, 7530, 2009); or other suitable non-optical detection methods.

Alignment and/or compilation of sequence results obtained from the image stacks produced as generally described above utilizes look-up tables that take into account possible sequences changes (due, e.g., to errors, mutations, etc.). Essentially, sequencing results obtained as described herein are compared to a look-up type table that contains all possible reference sequences plus 1 or 2 base errors.

In some embodiments, a plurality of nucleic acid molecules being sequenced are bound to a solid support. To immobilize the nucleic acid on a solid support, a capture sequence/universal priming site can be added at the 3' and/or 5' end of the template. The nucleic acids may be bound to the solid support by hybridizing the capture sequence to a complementary sequence covalently attached to the solid support. The capture sequence (also referred to as a universal capture sequence) is a nucleic acid sequence complimentary to a sequence attached to a solid support that may dually serve as a universal primer. In some embodiments, the capture sequence is polyN$_n$, where N is U, A, T, G, or C, e.g., 20-70, 40-60, e.g., about 50. For example, the capture sequence could be polyT$_{40-50}$ or its complement. As an alternative to a capture sequence, a member of a coupling pair (such as, e.g., antibody/antigen, receptor/ligand, or the avidin-biotin pair as described in, e.g., U.S. Patent Application No. 2006/0252077) may be linked to each fragment to be captured on a surface coated with a respective second member of that coupling pair.

Hypermethylation Linked to Disease

Numerous examples of hypermethylated genes that have been linked to various types of cancer have been identified. Examples of hypermethylated genes that have been linked with susceptibility to or incidence of colorectal cancer include, for example, FOXE1, SOX17, SYNE1, BOLL, CABYR, EFEMP1, FBLN2, FOXL2, GNB4, GSTM3, HoxD1, Jph3, Neuralized (NEURL), PPP1R14a, TP53AP1, RAB32, APC2, GPNMB, MMP2, EVL, STARD8, PTPRD, CD109, LGR6, RET, CHD5, RNF182, ICAM5, ARMCX2, CBR1, DDX43, DMRTB1, FBLN2, HIST2H2AA, ICAM1, LY6K, NEF3, POMC, STK31, SYCP3, TCL1A, TFPI-2, TLR2, UCHL1, ZFP42, ASCL2, ATP8A2, CTAG2, EPHA4, FANCF, FOXQ1, HUS1B, JAM3, LEF1, MOV10L1, NPPB, PWWP1, RASSF5, REC8L1, SALL4, BEX1, BNIP3, CCK, CDX1, CNN3, CXX1, IRX4, MC5R, RSNL2, SMARCA3, SPON1, SYT6, TRPC3, TSPYL6, ZNF345, DKK3, ZNF655, B4GALT1, C10orf119, C10orf13, CBR1, COPS4, COVA1, CSRP1, DARS, DNAJC10, FKBP14, FN3KRP, GANAB, HUS1, KLF11, MRPL4, MYLK, NELF, NETO2, PAPSS2, RBMS2, RHOB, SECTM1, SIRT2, SIRT7, SLC35D1, SLC9A3R1, TTRAP, TUBG2, FLJ20277, MYBL2, GPR116, QSMR, PC4, SLC39A4, UBE3A, PDLIM3, UBE21, or any combination thereof.

Examples of hypermethylated genes that have been linked with susceptibility to or incidence of prostate cancer include, for example, GSTP1, APC, PTGS2, T1G1, EDNRB, RASS1a, GSTP1, APC, PTGS2, T1G1, EDNRB, RASS1a, CD3D, APOC1, NBL1, ING4, LEF1, CENTD3, MGC15396, FKBP4, PLTP, TFAP2A, ATXN1, BMP2, ENPEP, MCAM, SSBP2, PDLIM3, NDP, or any combination thereof.

Examples of hypermethylated genes that have been linked with susceptibility to or incidence of breast cancer include, for example, PITX2, PITX2, BACH1, CKMT, GALE, HMG20B, KRT14, OGDHL, PON2, SESN1, KIF1A (kinesin family member 1A) PDLIM3, MAL (T cell proliferation protein), or any combination thereof.

Examples of hypermethylated genes that have been linked with susceptibility to or incidence of lung cancer include, for example, p161NK4a, APC, TMS1, RASSF1, DAPK, PRSS3 (serine protease family member-trypsinogen IV—a putative tumor suppressor gene), human DAB2 interactive protein gene, apoptosis-associated speck-lick protein containing a CARD, p16, FHIT, H-cadherin, RARβ, RARB2, PHKA2, CBR3, CAMK4, HOXB5, ZNF198, RGS4, RBM15B, PDLIM3, PAK3, PIGH, TUBB4, NISCH or any combination thereof.

Examples of hypermethylated markers that have been shown to be associated with susceptibility to or incidence of gastrointestinal cancer include, without limitation, NDRG4/NDRG2 subfamily gene, GATA4, OSMR, GATA5, SFRP1, ADAM23, JPH3, SFRP2, APC, MGMT, TFPI2, BNIP3, FOXE1, SYNE1, SOX17, PHACTR3, JAM3, or any combination thereof.

Examples of hypermethylated genes that have been linked with susceptibility to or incidence of cervical cancer include, for example, ESR1, DAP-kinase, APC, TIMP-3, RAR-beta, CALCA, TSLC1, TIMP-2, DcR1, DcR2, BRCA1, p15, Rassf1A, MLH1, MGMT, PDCD4, TFPI2, ARMC7, TRM-HUMAN, OGDHL, PTGS2, CDK6, GPR39, HMGN2, C130RF18, ASMTL, DLL4, NP-659450.1, NP-078820.1, CLU, HPCA, PLCG2, RALY, GNB4, CCNA1, NPTX1, C90RF19, or any combination thereof.

Nucleic acid sequences and the corresponding amino acid sequences for each of the genes referenced herein are well known and have been published in sequence databases that are freely accessible to the general public such as the GenBank, the National Institutes of Health genetic sequence database, and Protein, which includes a collection of sequences from several sources, including translations from annotated coding regions in GenBank, RefSeq and TPA, as well as records from SwissProt, PIR, PRF, and PDB. Thus, such sequences are readily available to the skilled artisan for use in designing chimeric primers and chimeric probes having sequences specific for the DNA encoding such genes for use in the methods of the invention.

EXAMPLES

Example 1

Amplification of methylation sites in TWIST

Two primers, Forward A4 (FORA4) (SEQ ID NO. 25: 3'-TTT*GAT*GTTTTTTGGGTTG) and Reverse SM REV1 (SEQ ID NO. 26: 3'-GAGGGAAGGGGGAGGG) were prepared as shown in FIG. 5. The primers were complimentary to sequences adjacent to regions of TWIST that are known to have potential methylation sites. As shown in FIG. 5, there were 14 CpG islands between the primer sites. Some or all of the CpG islands could be methylated in a sample, and the methylation pattern may be indicative of a disease, e.g., cancer.

Forward primer FORA4 contains two abasic regions, allowing it to specifically hybridize with methylated or unmethylated template DNA. The corresponding mismatch primer, wherein "*" is replaced with "N" could be prepared using the methods described herein, but is not shown. Reverse primer SM REV1 did not contain any abasic (or mismatched) sites.

Using the disclosed primers, amplicons were produced and amplified using qPCR. FIG. 6 shows the amplification efficiency of the primers as a function of concentration. As shown in FIG. 6, using as little as 300 nM primers, it is possible to reliably detect the amplicons using only cycles of PCR, and regardless of the methylation pattern of the original template. Analysis of the amplicons, e.g., via deep sequencing, will give information about the methylation of this region of TWIST.

Example 2

Amplification of Methylation Sites in NID

Two primers, Forward A3 (FORA3) (SEQ ID NO. 27: 3'-TTTTTTTATTGGGGTTGTTT) and Reverse SM REV3 (SEQ ID NO. 28: 3'-GTTGTGGTTTTAATAGGTTG) were prepared as shown in FIG. 7. The primers were complimentary to sequences adjacent to regions of NID that are known to have potential methylation sites. As shown in FIG. 7, there were 13 CpG islands between the primer sites. Some or all of the CpG islands could be methylated in a sample, and the methylation pattern may be indicative of a disease, e.g., cancer.

Forward primer FORA3 contains one mismatch region (shown as lower-case or underlined "G"), allowing it to specifically hybridize with methylated or unmethylated template DNA. The corresponding abasic primer, wherein "G" is replaced with "*" could be prepared using the methods described herein, but is not shown. Reverse primer SM REV3 did not contain any mismatched (or abasic) sites.

Figure 8:
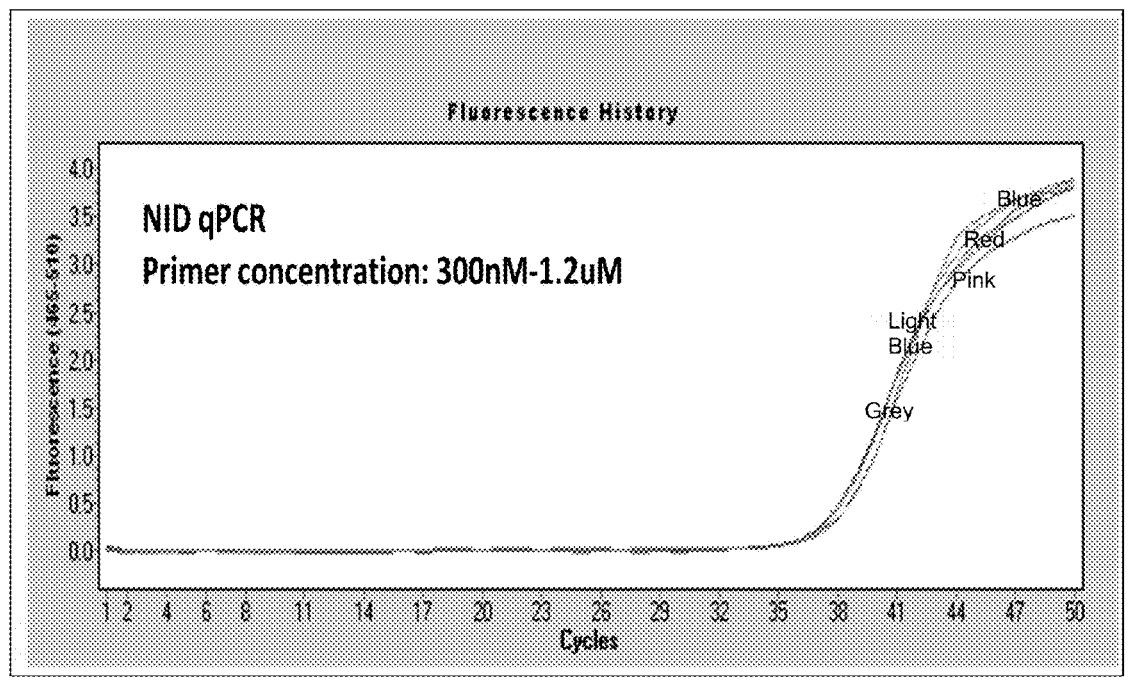
FIG. 8 shows fluorescence intensity due to production of amplification products as a function of the concentration of the primers shown in FIG. 7.

Using the disclosed primers, amplicons were produced and amplified using qPCR. FIG. 8 shows the amplification efficiency of the primers as a function of concentration. As shown in FIG. 8, using as little as 300 nM primers, it is possible to reliably detect the amplicons using only 38 cycles of PCR, and regardless of the methylation pattern of the original template. Analysis of the amplicons, e.g., via deep sequencing, will give information about the methylation of this region of NID.

INCORPORATION BY REFERENCE

References and citations to other documents, such as patents, patent applications, patent publications, journals, books, web contents, have been made throughout this disclosure. All documents are hereby incorporated herein by reference in their entirety for all purposes.

EQUIVALENTS

The invention may be embodies in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced from within.

The invention claimed is:

1. A primer that it is able to specifically hybridize to either a methylated or an unmethylated CpG site of a template nucleic acid, wherein the primer comprises an abasic region that interacts with the methylated or the unmethylated CpG site of the template nucleic acid wherein the primer comprises the nucleotide sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 or SEQ ID NO: 12.

2. The primer according to claim 1, wherein the abasic region spans at least one base of the template.

3. The primer according to claim 1, wherein the abasic region is covalently linked to a guanine moiety.

4. The primer according to claim 1, wherein the abasic region comprises a moiety selected from the group consisting of:

O-dimethoxytrityl-1',2'-dideoxyribose-3'-[(2-cyanoethyl)-(N,N-diisopropyl)]-phosphoramidite;

O-dimethoxytrityl-1'-methoxy-2'-dideoxyribose-3'-[(2-cyanoethyl)-(N,N-diisopropyl)]-phosphoramidite;

[4-(4,4'-Dimethoxytrityloxy)butyramidomethyl]-1-(2-nitrophenyl)-ethyl]-2-cyanoethyl-(N,N-diisopropyl)-phosphoramidite;

O-Dimethoxytrityl-1'-Deoxyribose-2'-O-Triisopropylsilyloxymethyl-3'-[(2-cyanoethyl)-(N,N-diisopropyl)]-phosphoramidite;

(4,4'-Dimethoxytrityloxy)-dodecyl-1-[(2-cyanoethyl)-(N,N-diisopropyl)]-phosphoramidite);

O-Dimethoxytritylhexaethyleneglycol,1-[(2-cyanoethyl)-(N,N-diisopropyl)]-phosphoramidite;

O-Dimethoxytrityl-triethyleneglycol,1-[(2-cyanoethyl)-(N,N-diisopropyl)]-phosphoramidite; and 3-(4,4'-Dimethoxytrityloxy)propyl-1-[(2-cyanoethyl)-(N,N-diisopropyl)]-phosphoramidite.

5. The primer according to claim 1, wherein the primer comprises at least one mismatched nucleotide that has similar annealing characteristics to both uracil and cytosine such that the primer hybridizes to either the methylated or the unmethylated CpG site of the template nucleic acid.

6. The primer according to claim 5, wherein the primer comprises the nucleotide sequence selected from the group consisting of: SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24.

7. The primer according to claim 1, wherein the primer further comprises an adaptor sequence.

8. The primer according to claim 7, wherein the adaptor sequence comprises a homopolymer region.

\* \* \* \* \*

SEQUENCE LISTING

<160> NUMBER OF SEQ ID NOS: 28

<210> SEQ ID NO 1
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (8)..(8)
<223> OTHER INFORMATION: "n" is an abasic region spanning one base of
      the template
<220> FEATURE:
<221> NAME/KEY: misc_feature
<222> LOCATION: (10)..(10)
<223> OTHER INFORMATION: "n" is an abasic region spanning one base of
      the template

<400> SEQUENCE: 1
ggattggngn tattgttggg gtag                                              24

<210> SEQ ID NO 2
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (14)..(14)
<223> OTHER INFORMATION: "n" is an abasic region spanning one base of
      the template
<220> FEATURE:
<221> NAME/KEY: misc_feature
<222> LOCATION: (18)..(18)
<223> OTHER INFORMATION: "n" is an abasic region spanning one base of
      the template

<400> SEQUENCE: 2
gttgggtttt ttgntagntt                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (5)..(5)
<223> OTHER INFORMATION: "n" is an abasic region spanning one base of
      the template
<220> FEATURE:
<221> NAME/KEY: misc_feature
<222> LOCATION: (11)..(11)
<223> OTHER INFORMATION: "n" is an abasic region spanning one base of
      the template

<400> SEQUENCE: 3
gttgnggggg nttgggattg                                                   20

<210> SEQ ID NO 4
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)

```
<223> OTHER INFORMATION: "n" is an abasic region spanning one base of
      the template
<220> FEATURE:
<221> NAME/KEY: misc_feature
<222> LOCATION: (6)..(6)
<223> OTHER INFORMATION: "n" is an abasic region spanning one base of
      the template
<220> FEATURE:
<221> NAME/KEY: misc_feature
<222> LOCATION: (16)..(16)
<223> OTHER INFORMATION: "n" is an abasic region spanning one base of
      the template
<220> FEATURE:
<221> NAME/KEY: misc_feature
<222> LOCATION: (19)..(19)
<223> OTHER INFORMATION: "n" is an abasic region spanning one base of
      the template

<400> SEQUENCE: 4
ggnagnggaa ggaggntgnt t                                              21

<210> SEQ ID NO 5
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (4)..(4)
<223> OTHER INFORMATION: "n" is an abasic region spanning one base of
      the template
<220> FEATURE:
<221> NAME/KEY: misc_feature
<222> LOCATION: (15)..(15)
<223> OTHER INFORMATION: "n" is an abasic region spanning one base of
      the template

<400> SEQUENCE: 5
gggnggagga ttggnggga                                                 19

<210> SEQ ID NO 6
<211> LENGTH: 22
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: "n" is an abasic region spanning one base of
      the template
<220> FEATURE:
<221> NAME/KEY: misc_feature
<222> LOCATION: (13)..(13)
<223> OTHER INFORMATION: "n" is an abasic region spanning one base of
      the template
<220> FEATURE:
<221> NAME/KEY: misc_feature
<222> LOCATION: (17)..(17)
<223> OTHER INFORMATION: "n" is an abasic region spanning one base of
      the template
<220> FEATURE:
<221> NAME/KEY: misc_feature
<222> LOCATION: (21)..(21)
<223> OTHER INFORMATION: "n" is an abasic region spanning one base of
      the template

<400> SEQUENCE: 6
tgntggattg ggnttgntgg nt                                             22

<210> SEQ ID NO 7
<211> LENGTH: 17
<212> TYPE: DNA
```

-continued

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(7)
<223> OTHER INFORMATION: "n" is an abasic region spanning one base of
      the template

<400> SEQUENCE: 7 gttgggnntta tttttt                                                    17

<210> SEQ ID NO 8
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: "n" is an abasic region spanning one base of
      the template
<220> FEATURE:
<221> NAME/KEY: misc_feature
<222> LOCATION: (24)..(24)
<223> OTHER INFORMATION: "n" is an abasic region spanning one base of
      the template

<400> SEQUENCE: 8
nttttatttt gaggaatttt tggng                                           25

<210> SEQ ID NO 9
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: "n" is an abasic region spanning one base of
      the template
<220> FEATURE:
<221> NAME/KEY: misc_feature
<222> LOCATION: (20)..(20)
<223> OTHER INFORMATION: "n" is an abasic region spanning one base of
      the template

<400> SEQUENCE: 9
ggngatgggg tttggaatgn t                                               21

<210> SEQ ID NO 10
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: "n" is an abasic region spanning one base of
      the template
<220> FEATURE:
<221> NAME/KEY: misc_feature
<222> LOCATION: (16)..(16)
<223> OTHER INFORMATION: "n" is an abasic region spanning one base of
      the template

<400> SEQUENCE: 10
gntttaaggg aaatgnga                                                   18
```

```
<210> SEQ ID NO 11
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (6)..(6)
<223> OTHER INFORMATION: "n" is an abasic region spanning one base of
      the template
<220> FEATURE:
<221> NAME/KEY: misc_feature
<222> LOCATION: (12)..(12)
<223> OTHER INFORMATION: "n" is an abasic region spanning one base of
      the template
<220> FEATURE:
<221> NAME/KEY: misc_feature
<222> LOCATION: (15)..(15)
<223> OTHER INFORMATION: "n" is an abasic region spanning one base of
      the template

<400> SEQUENCE: 11
gttggngtga gnggngat                                                 18

<210> SEQ ID NO 12
<211> LENGTH: 17
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: "n" is an abasic region spanning one base of
      the template
<220> FEATURE:
<221> NAME/KEY: misc_feature
<222> LOCATION: (5)..(5)
<223> OTHER INFORMATION: "n" is an abasic region spanning one base of
      the template

<400> SEQUENCE: 12
ggngngggat ggttgga                                                  17

<210> SEQ ID NO 13
<211> LENGTH: 24
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (8)..(8)
<223> OTHER INFORMATION: "n" is a single mismatched base
<220> FEATURE:
<221> NAME/KEY: misc_feature
<222> LOCATION: (10)..(10)
<223> OTHER INFORMATION: "n" is a single mismatched base

<400> SEQUENCE: 13
ggattggngn tattgttggg gtag                                          24

<210> SEQ ID NO 14
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (14)..(14)
<223> OTHER INFORMATION: "n" is a single mismatched base
<220> FEATURE:
```

```
<221> NAME/KEY: misc_feature
<222> LOCATION: (18)..(18)
<223> OTHER INFORMATION: "n" is a single mismatched base

<400> SEQUENCE: 14
gttgggtttt ttgntagntt                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (5)..(5)
<223> OTHER INFORMATION: "n" is a single mismatched base
<220> FEATURE:
<221> NAME/KEY: misc_feature
<222> LOCATION: (11)..(11)
<223> OTHER INFORMATION: "n" is a single mismatched base

<400> SEQUENCE: 15
gttgnggggg nttgggattg                                                    20

<210> SEQ ID NO 16
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: "n" is a single mismatched base
<220> FEATURE:
<221> NAME/KEY: misc_feature
<222> LOCATION: (6)..(6)
<223> OTHER INFORMATION: "n" is a single mismatched base
<220> FEATURE:
<221> NAME/KEY: misc_feature
<222> LOCATION: (16)..(16)
<223> OTHER INFORMATION: "n" is a single mismatched base
<220> FEATURE:
<221> NAME/KEY: misc_feature
<222> LOCATION: (19)..(19)
<223> OTHER INFORMATION: "n" is a single mismatched base

<400> SEQUENCE: 16
ggnagnggaa ggaggntgnt t                                                  21

<210> SEQ ID NO 17
<211> LENGTH: 19
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (4)..(4)
<223> OTHER INFORMATION: "n" is a single mismatched base
<220> FEATURE:
<221> NAME/KEY: misc_feature
<222> LOCATION: (15)..(15)
<223> OTHER INFORMATION: "n" is a single mismatched base

<400> SEQUENCE: 17
gggnggagga ttggnggga                                                     19

<210> SEQ ID NO 18
<211> LENGTH: 22
<212> TYPE: DNA
```

```
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: "n" is a single mismatched base
<220> FEATURE:
<221> NAME/KEY: misc_feature
<222> LOCATION: (13)..(13)
<223> OTHER INFORMATION: "n" is a single mismatched base
<220> FEATURE:
<221> NAME/KEY: misc_feature
<222> LOCATION: (17)..(17)
<223> OTHER INFORMATION: "n" is a single mismatched base
<220> FEATURE:
<221> NAME/KEY: misc_feature
<222> LOCATION: (21)..(21)
<223> OTHER INFORMATION: "n" is a single mismatched base

<400> SEQUENCE: 18
tgntggattg ggnttgntgg nt                                          22

<210> SEQ ID NO 19
<211> LENGTH: 17
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (7)..(7)
<223> OTHER INFORMATION: "n" is a single mismatched base

<400> SEQUENCE: 19
gttgggntta tttttt                                                 17

<210> SEQ ID NO 20
<211> LENGTH: 25
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (1)..(1)
<223> OTHER INFORMATION: "n" is a single mismatched base
<220> FEATURE:
<221> NAME/KEY: misc_feature
<222> LOCATION: (24)..(24)
<223> OTHER INFORMATION: "n" is a single mismatched base

<400> SEQUENCE: 20
nttttatttt gaggaatttt tggng                                       25

<210> SEQ ID NO 21
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: "n" is a single mismatched base
<220> FEATURE:
<221> NAME/KEY: misc_feature
<222> LOCATION: (20)..(20)
<223> OTHER INFORMATION: "n" is a single mismatched base

<400> SEQUENCE: 21
ggngatgggg tttggaatgn t                                           21
```

```
<210> SEQ ID NO 22
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (2)..(2)
<223> OTHER INFORMATION: "n" is a single mismatched base
<220> FEATURE:
<221> NAME/KEY: misc_feature
<222> LOCATION: (16)..(16)
<223> OTHER INFORMATION: "n" is a single mismatched base

<400> SEQUENCE: 22
gntttaaggg aaatgnga                                                 18

<210> SEQ ID NO 23
<211> LENGTH: 18
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (6)..(6)
<223> OTHER INFORMATION: "n" is a single mismatched base
<220> FEATURE:
<221> NAME/KEY: misc_feature
<222> LOCATION: (12)..(12)
<223> OTHER INFORMATION: "n" is a single mismatched base
<220> FEATURE:
<221> NAME/KEY: misc_feature
<222> LOCATION: (15)..(15)
<223> OTHER INFORMATION: "n" is a single mismatched base

<400> SEQUENCE: 23
gttggngtga gnggngat                                                 18

<210> SEQ ID NO 24
<211> LENGTH: 17
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (3)..(3)
<223> OTHER INFORMATION: "n" is a single mismatched base
<220> FEATURE:
<221> NAME/KEY: misc_feature
<222> LOCATION: (5)..(5)
<223> OTHER INFORMATION: "n" is a single mismatched base

<400> SEQUENCE: 24
ggngngggat ggttgga                                                  17

<210> SEQ ID NO 25
<211> LENGTH: 21
<212> TYPE: DNA
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (14)..(14)
<223> OTHER INFORMATION: "n" is an abasic region spanning one base of
      the template
<220> FEATURE:
<221> NAME/KEY: misc_feature
<222> LOCATION: (18)..(18)
<223> OTHER INFORMATION: "n" is an abasic region spanning one base of
```

-continued

```
                the template

<400> SEQUENCE: 25
gttgggtttt ttgntagntt t                                              21

<210> SEQ ID NO 26
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 26 gggagggga agggag                                                     16

<210> SEQ ID NO 27
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 27
tttgttgggg ttattttttt                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 28
gttggataat tttggtgttg                                                20
```